US006207439B1

(12) United States Patent
Liau et al.

(10) Patent No.: US 6,207,439 B1
(45) Date of Patent: Mar. 27, 2001

(54) PURIFICATION OF JAPANESE ENCEPHALITIS VIRUS

(75) Inventors: Ming-Yi Liau; Ruwen Jou; Aih-Jing Chiou, all of Taipei (TW)

(73) Assignee: Center for Disease Control, Taipei (TW)

( * ) Notice: Subject to any disclaimer, the term of this patent is extended or adjusted under 35 U.S.C. 154(b) by 0 days.

(21) Appl. No.: 08/823,989

(22) Filed: Mar. 25, 1997

(51) Int. Cl.$^7$ ................................ C12N 7/02; C12N 7/04; C12N 7/00
(52) U.S. Cl. .................. 435/239; 435/235.1; 435/236; 424/218.1
(58) Field of Search ................................ 435/235.1, 236, 435/239; 514/885; 424/218.1

(56) References Cited

U.S. PATENT DOCUMENTS 4,725,546 * 2/1988 Sakamoto et al. .................... 435/239

FOREIGN PATENT DOCUMENTS

| 2737412 | 8/1995 | (FR) . |
| 2269820 | 8/1991 | (GB) . |
| 1522494 * | 11/1994 | (RU) . |
| WO 97/04803 | 2/1997 | (WO) . |

OTHER PUBLICATIONS

Smith, J. Virological Meth., 16:263–269, 1987.*
Bengtsson et al., Biochim. Biophys. Acta, 79:399–406, 1964.*
A. S. Michaels, in Progress in Separation And Purification, vol. 1, Ed. E.S. Perry, Interscience Publishers, NY, pp. 297–334, 1968.*
Florian Horaud, Viral Vaccines and Residual Cellular DNA, *Biologicals,* (1995) 23, pp. 225–228.
Bishop, et al., Rapid and Efficient Purification of Hepatitis A Virus From Cell Culture, *Journal of Virological Methods,* 47 (1994) pp. 203–216.
Dong S, et al.; A Domestic Cell Bioreactor And Its Application In Virus Culture; *Chin J. Biotechnol* 9 (2): pp. 117–121 (1993); and Wang D., et al. Studies on High–Density Cultivation of Vero Cells With Biosilon Solid Microcarrier, *Chin J. Biotechnol* 12 (2): pp. 119–129 (1996).

T. Lee, et al.; Preparation of Japanese Encephalitis Virus Nonstructural Protein NSI Obtained From Culture Fluid of JEV–Infected Vero Cells; *Arch Virol* (1991) 116: pp. 253–260.

Gupta et al.; An Efficient Method For Production of Purified Inactivated Japanese Encephalitis Vaccine From Mouse Brains; *Vaccine,* vol. 9, Dec. 1991, pp. 865–867.

van Wezel, et al.; Large–Scale Concentration and Purification of Virus Suspension from Microcarrier Culture For The Preparation of Inactivated Virus Vaccines;

Okuda et al.; Purification of Japanese Encephalitis Virus Vaccine By Zonal Centrifugation; *Journal of Clinical Microbiology,* Jan. 1975, pp. 96–101.

Igarashi et al.; Purification of Japanese Encephalitis Virus Grown in BHK21 and Singh's Aedes Albopictus Cells By Polyethylene Glycol Precipitation, *Biken Journal,* vol. 16, 1973, pp. 67–73.

Takaku, et al.; Japanese Encephalitis Purified Vaccine, *Biken Journal,* vol. 11, 1968, pp. 25–39.

* cited by examiner

*Primary Examiner*—Jon P. Weber
*Assistant Examiner*—Janet M. Kerr
(74) *Attorney, Agent, or Firm*—Alston & Bird LLP

(57) ABSTRACT

This invention provides a process for large-scale purification of living Japanese encephalitis virus (JEV) suitable for use in vaccine preparation from a JEV source, including a JEV-infected cell culture and a JEV-infected mouse brain. The process includes the following steps:

(a) obtaining a sample from a JEV-infected mouse brain or a JEV-infected cell culture, (b) subjecting the sample to a preliminary separation to remove cell and cell debris from the sample of step (a), (c) concentrating the sample from step (b) by ultrafiltration to remove substances having molecular weight below 100 kDa, and (d) subjecting the sample concentrate to gel filtration to obtain a substantially pure fraction of JEV.

17 Claims, 8 Drawing Sheets

FIG. 1A

Purification of Japanese encephalitis virus on Sepharose CL-6B

Purification of Japanese Encephalitis Virus on POROS HQ/M

Channel A

JE virus ↓

FIG.1B

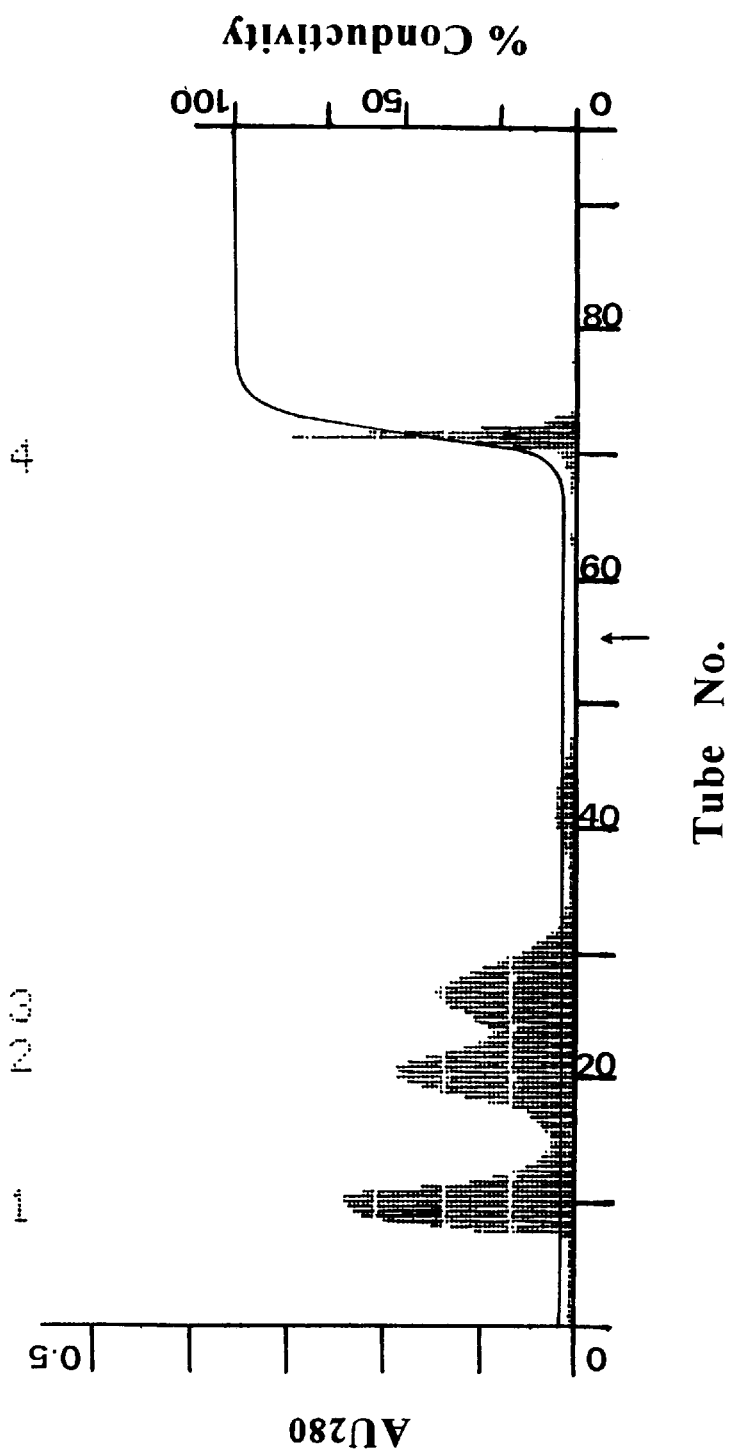
FIG.1C Purification of Japanese encephalitis virus on Cellufine Sulfate Reproducible Performance of Gel Filtration on Sepharose CL-6B The kinetic curves of JEV inactivation by formalin.

FIG.3

Purity of Japanese Encephalitis Virus

FIG.5

PURIFICATION OF JAPANESE ENCEPHALITIS VIRUS

BACKGROUND OF THE INVENTION

1. Field of the Invention

This invention relates to a process for purification of Japanese encephalitis virus (JEV), in particular a large-scale process suitable for use in vaccine preparation.

2. Description of the Related Art Japanese encephalitis virus (JEV), a spherical RNA virus belonging to genus Flavivirus of virus family Flaviviridae, which is an important, severe, human pathogen which is spread through the vector mosquito, causing serious public health problems during summer time in the West Pacific and Southeast Asian Regions. The infection may result in permanent neurological or psychiatric injury or even death. The spread of the disease has been effectively controlled through vaccination. The vaccine employed is traditionally manufactured from isolated, purified and formalin-inactivated virus harvested from infected mouse brain tissue. To date, because of its relatively low cost and high efficacy, vaccinating children with inactivated JE vaccine remains the most effective means for the disease control of JE in many countries in the above-mentioned areas.

Unfortunately, the mouse brain-derived JE vaccine has the drawback of provoking allergic reaction easily in the human body upon repeated vaccination due to the presence of residual mouse tissue proteins which are difficult to remove away during purification procedures. For decades, efforts have been made and thereby several methods, including protamine sulfate precipitation (Ada, G. L., Anderson, S. G., and Abbot, A. J. (1961), Purification of Murray Valley encephalitis virus, *Gen. Microbiol.*, 24: 177–186; and Cheng, P.-Y. (1961), Purification, size and morphology of mosquito borne animal virus Semliki Forest encephalitis viruses, *Virology*, 14: 124–131), active carbon treatment (Steven, T. M., and Schlesinger, R. W. (1965), Studies on the nature of Dengue viruses 1. Correlation of particle density, infectivity and RNA content of type 2 virus, *Virology*, 27: 103–112), alcohol precipitation (Nakamura, J. (1969), Studies on the purified Japanese encephalitis vaccines, *NIBS Bull. Biol. Res.*, 8: 78–99), polyethylene glycol precipitation (Aizawa, C., Hasegawa, S., Cheng, C.-Y., and Yoshioka, I. (1980), Large-scale purification of Japanese encephalitis virus from infected mouse brain for preparation of vaccine, *APPl. Env. Microbiol.*, 39: 54–57), separation by hydroxyapatite column (Pfefferkorn, E. R., and Hunter, H. S. (1963), Purification and partial chemical analysis of Sindbis virus, *Virology*, 20: 433–445), sucrose density gradient sedimentation (Okuda, K., Ito, K., Miyake, K., Morita, M., Ogonuki, M. and Matsui, S. (1975), Purification of Japanese encephalitis vaccine by zonal centrifugation, *J. Clin. Microbiol.*, 1: 96–101), as well as various combinations of the above, were found to obtain vaccines with reasonable purities.

Although some successes have been seen in the above-discussed methods, the achievements employing these purification procedures are limited due to the remaining trace amounts of impurities originating from mouse brain myelin proteins, or the complexity of the procedures to be practically utilized. In addition, in order to meet the regulation promulgated by the WHO that the protein content in each dosage of JE vaccine should be less than 80 $\mu$g/ml, dilution of the JE vaccine has to be made occasionally and this will undesirably cause the virus titer in the vaccine to be lower than the reference vaccine. To solve these problems, certain JEV-susceptible established cell lines, such as BHK21, MK, Singh's *Aedes albopictus* (SA), Vero and C6/36 cells, have been employed in the culture of JE virus. It has been reported that high purity of JEV particles can be obtained from the above infected cells by the combined use of polyethylene glycol precipitation and sucrose gradient sedimentation (Akira, I., Takahisa, F., Fuyoko, S., Suranga, S., and Konosuke, F. (1973), Purification of Japanese encephalitis virus grown in BHK21 and Singh's *Aedes albopictus* cells by polyethylene glycol precipitation, *Biken J.*, 16: 67–73).

As liquid chromatography has been widely applied in the purification of biomolecules, cell organelles, and viral particles, Wezel et al. disclosed a sequential purification process comprising a combination of filter clarification, ultrafiltration, gel filtration, and anion-exchange liquid chromatography, in order to remove residual serum proteins in inactivated poliovirus and rabiesvirus suspensions harvested from infected cells (*Dev. Biol. Stand.*, 42: 65–69, 1978). However, it is unknown as to whether a similar method is applicable to the purification of other different viral particles, including JEV, without impairing the native structures and biological activities thereof.

Therefore, there is still a need to develop a less complicated and more efficient purification process under a physiological condition for the mass production of the JE virus for use in vaccine preparation.

SUMMARY OF THE INVENTION

One object of the invention is to provide a process for large-scale purification of living Japanese encephalitis virus (JEV) suitable for use in vaccine preparation from a JEV source, including JEV-infected cell cultures and JEV-infected mouse brains. The process comprises the following steps:

(a) obtaining a sample from JEV-infected mouse brains or JEV-infected cell cultures, (b) subjecting said sample to a preliminary separation to remove cell and cell debris from the sample of step (a), (c) concentrating said sample from step (b) by ultrafiltration to remove substances having a molecular weight below 100 kDa, and (d) subjecting the sample concentrate to gel filtration to obtain a substantially pure fraction of JEV.

With the present process, at least 95%, preferably at least 99%, of the contaminating proteinaceous substances are removed from the virus sample, whilst the viral particle still remains substantially intact without losing its infectivity. In addition, the present process can achieve a virus recovery yield of at least 80%, and more preferably 90%.

Another object of the present invention is to provide a process for purification of live JEV in high recovery yield and high purity, which comprises the three steps of microfiltration, ultrafiltration and gel filtration.

This invention also provides a JEV vaccine, which is prepared by inactivating the JEV obtained from the present process with an inactivation agent, e.g. formalin and binary ethyleneimide (BEI). Since the JE vaccine according to the present invention is of higher purity than the currently widely used mouse-brain vaccine and has no significant loss in antigenicity, it is suitable for use in the preparation of multi-valent vaccine, such as DPT-JE, DPT-HBV-JE and so forth.

Features and advantages of the present invention will become apparent from the following detailed description of the preferred embodiments and examples, with reference to the accompanying drawings, of which:

BRIEF DESCRIPTION OF THE DRAWINGS

FIGS. 1A–1C show the fractionation results from the purification of JE virus by gel filtration, ion exchange and affinity chromatography, respectively.

FIG. 3 shows the variations of JE virus infectivity and mouse survival rate along the course of the inactivation with formalin. Viral samples of the original harvest (RB-ORI), post-ultrafiltration (RB-UF), and post-CL-6B gel filtration (RB-CL-6B) were treated with 0.05% (v/v) formalin for inactivation. The residual virus infectivity was measured by both plaque assay and IC challenge test.

FIG. 5 is an electrophoresis depicting the relative purity of JE virus preparations at each purification step by silver staining after SDS-PAGE, in which lane 1 is molecular weight marker (Pharmacia Biotech); lane 2 is culture medium; lane 3 is the virus harvest; lane 4 is the microfiltrated virus; lane 5 is the ultrafiltrated virus; lane 6 is the LC-purified virus; lane 7 is NIPM mouse brain JE vaccine; and lane 8 is Kitasato Institute vaccine.

In FIG. 6A, lane 1: the LMW marker (Pharmacia Biotech); lane 3: BSA, lane 4: original harvest, RB48 20X; lane 5: RB48 20X→SEPHAROSE CL-6B peak I; lane 6: RB48 20X→SEPHAROSE CL-6B peak II; lane 7: RB48 20X→SEPHAROSE CL-6B peak III; lane 8: RB48 20X→SEPHAROSE CL-6B peak IV; lane 9: the Biken vaccine; and lane 10: the Kitasato Institute vaccine. In FIG. 6B, lanes 1 and 10: NOVEX Mark 12 (Novel Experimental Technology); lane 2: BSA; lane 5: RB48 20X→CL-6B:peak I; lane 6: RB48 20X→CL-6B:peak II; lane 7: RB48 20X→CL-6B:peak III; lane 8: RB48 20X→CL-6B:peak IV; and lane 9: RB48 20X.

DETAILED DESCRIPTION OF THE PREFERRED EMBODIMENTS

Figure 2:
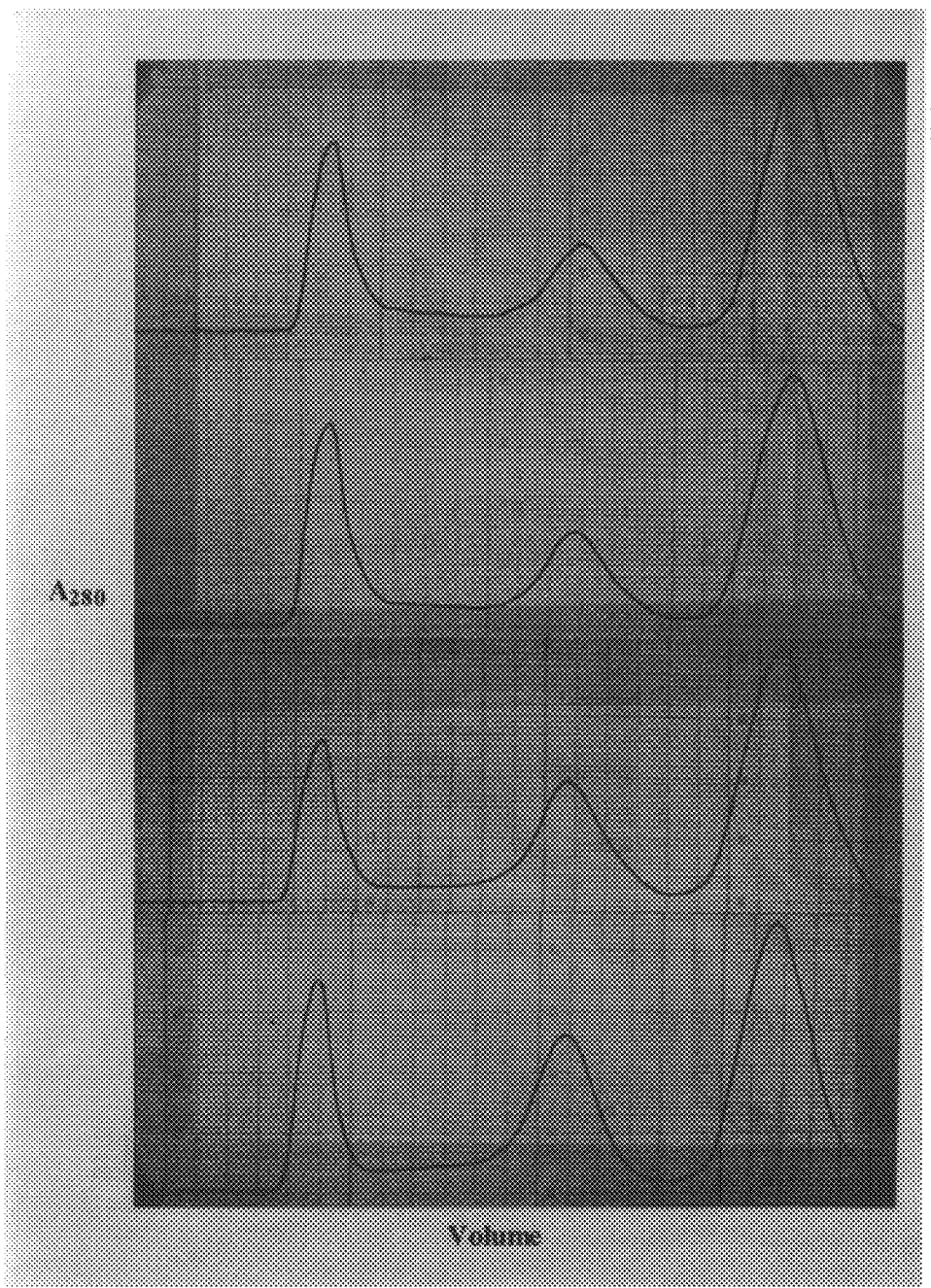
FIG. 2 shows the excellent reproducibility of the gel filtration in the purification of JE virus.

According to the present invention, the sources of the JE virus for purification may be JEV-infected mouse brains and JEV-infected cell cultures. For cell culture sources, suitable cell lines for the culture of JE virus include BHK21, MK, SA, Vero, C6/36 cells and the like. The whole culture, including the JEV infected cultured cells and the culture medium, can be harvested and directly subjected to the purification process of the present invention. For mouse brain sources, samples from JEV infected mouse brains are firstly subjected to a preliminary purification treatment using known procedures, such as ethanol precipitation and protamine sulfate precipitation, and the obtained supernatants are then ready for subjecting to the purification steps of the present process.

According to the present invention, the preliminary separation of virus particles from cells and cell debris is conventionally done through centrifugation within a range of 8,000–20,000×g. Preferably, the separation is conducted with microfiltration, and more preferably, with the use of a 0.45 μm filtration membrane.

In a preferred embodiment of the present process, subsequent to the microfiltration, ultrafiltration is conducted with the use of an appropriate filter membrane to achieve the effects of clarification, concentration, buffer exchange and fractionation of the virus sample. The filter membrane to be employed in the ultrafiltration has a molecular weight cutoff value smaller than that of JE virus, e.g. a filter membrane with a cutoff value of 100 kDa, 1000 kDa or 3000 kDa, so that at least 90% of the undesired contaminating proteinaceous substances present in the JEV sample are removed. Preferably, the ultrafiltration is conducted with use of recirculation filtration and the flow rate thereof is at 1–3 l/min, more preferably at 1 l/min.

In a preferred embodiment of the present process, the step of ultrafiltration is followed by the step of gel filtration. The gel filtration is preferably conducted with a column packed with a gel matrix having the capability to separate substances with a molecular weight within the range of 10 kDa–4000 kDa. The gel matrix may be SEPHAROSE CL-6B, CL-4B, CL-2B, 6B, 4B or 2B, SEPHACRYL S-400 or S-300, SUPEROSE 6 or ULTROGEL A2, A4 or A6, where SEPHAROSE CL-6B is preferred. Preferably, the gel filtration is carried out by using the Pharmacia FPLC system or BioRad Perfusion Chromatography Workstation with 1/75 M phosphate buffer containing 0.85% NaCl (pH 7.4) as the elution buffer.

EXAMPLE

I. Materials and Methods

A. Materials

Virus: The tested Beijing strain JE virus samples include the Reference mouse-brain vaccine (Batch No. 184P) obtained from the National Institute of Health (NIH), Japan, and also from the mouse brains and cell cultures prepared in the National Institute of Preventive Medicine, Taipei, Taiwan, R.O.C.

Mouse: Mice used in IC challenge test are those of SPF ICR strain of 12–14 g body weight or about 8 weeks old.

B. General Assay

Protein Determination

The protein content is determined by either the Bradford or the Lowry method (Bradford, M. (1976), A rapid and sensitive method for the quantification of microgram quantities of protein utilizing the principle of protein-dye binding, Anal. Biochem., 72, 248–254; and Lowry, O. H., Rosenbrough, N. J., Farr, A. L., and Randall, R. J. (1951), Protein measurement with the Folin-phenol reagent, J. Biol. Chem., 193, 265–275), in which bovine serum albumin (BSA) is used as standard and commercial mouse-brain vaccine is used as reference.

Quantification of BSA by ELISA

The ELISA assay is conducted as described by Edevag, G., Eriksson, M., Granstrom, M. (1986) in "The development and standardization of an ELISA for ovalbumin determination in Influenza vaccines," J. Biol. Stand. 14, 223–230, and by Granstrom, M., Eriksson, M., Edevag, G. (1987) in "A sandwich ELISA for bovine serum in viral vaccines," J. Biol. Stand., 15, 193–197, which references are incorporated herein by reference.

Initially, a 100 μl of rabbit anti-BSA antibodies, which is diluted to 1:10,000 with the use of a freshly prepared coating buffer (0.05 M sodium carbonate buffer, pH 9.5–9.7), is added to each well of a 96-well microtitration plate. The plate is covered with a cover lid and incubated at 4° C. overnight. Thereafter, prior to each step, the wells are washed with 175 μl of PBST (0.015 M phosphate-buffered saline containing 0.05% Tween 20, pH 7.4) by an ELISA autowasher (Bio-Tek EL403) for five times, with shaking for 5 seconds.

A 100 μl of the aforementioned coating buffer containing 0.1% gelatin is added to each well and incubated at ambient temperature (around 27° C.) for 1 hour to block the non-specific protein binding sites and then repeatedly washed 5 times. The same goes after each step thereafter.

The test samples are diluted with PBST to various concentrations and each well is added with 100 μl of an appropriately diluted sample (in triplicate for every sample). The samples are allowed to stand at room temperature for 90 minutes.

A 100 μl of goat anti-BSA antibodies at a dilution of 1:10,000 in PBST is then added into each well, the wells are allowed to stand at room temperature for 90 minutes.

A 100 μl of alkaline phosphatase (AP) conjugated rabbit anti-goat IgG complexes at a dilution of 1:1000 in PBST is added into each well and incubated at room temperature for 90 minutes.

A substrate solution is prepared by dissolving 5 mg of p-nitrophenyl phosphate in 5 ml of 1 M diethanolamine, pH 9.8, and a 100 μl of the substrate solution is added into each well. The plate is placed in the dark for 40 minutes, before the $A_{405}$ absorbance is monitored by an ELISA reader (Molecular Devices, Emax).

SDS-PAGE and Western Blot

A 12.5% non-reducing SDS-PAGE (Laemmli, U. K. (1970), Cleavage of structural proteins during the assembly of the head of bacteriophage T4, *Nature*, 227, 680) is performed to check the purity of JE virus. Thereafter, the resulting gels are transferred onto a nitrocellulose (NC) paper (Towbin, H., Stachelin, T., Gordon, J. (1979), Electrophoretic transfer of proteins from polyacrylamide gels to nitrocellulose sheets: procedure and some applications, *Proc. Natl. Acad. Sci. USA,* 76, 4350). The NC paper is blocked with 1% gelatin in PBS for 30 minutes and then incubated with a primary antibody in PBS at 4° C. overnight. After the NC paper was washed 3 times with PBS containing 0.05% Tween 20, it is incubated with an AP-conjugated secondary antibody in PBS and allowed to react at room temperature for 1 hour. After washing 3 times, the NC paper is incubated with BCIP/NBT (5-bromo-4-chloro-3-indolyl-phosphate/ nitroblue tetrazolium) for 5 minutes.

Plague Assay

The plaque assay has been described by Oya, A., Kan, K., Kurokawa, M., Ishida, S. (1967) in "A new form of direct calculation of neutralizing antibody titer against Japanese encephalitis virus from plaque reduction rate on CE tissue culture," Tokyo: Japanese Encephalitis Vaccine Research Commission, 5–10, and by Read, L. J., Muench, H. (1938) in "A simple method of estimating fifty percent endpoints," *Am. J. HYQ.,* 27, 493–479, which are incorporated herein by reference.

Each well of a 6-well plate is inoculated with $8\times10^5$ BHK cells. The cells are incubated at 37° C. overnight in a $CO_2$ incubator until the wells were covered with a monolayer of cells. The cells are then incubated with 100 μl of the tested virus sample for 1 hour to allow the adsorption of virus to the cells. A 2 ml overlay medium is added into each well. After 72 hours, the cells are stained and the observed plaques are counted.

IC Challenge Test 10 mice (12–15 g) are challenged by injection with a virus sample (0.03 ml/mouse) into the brains thereof and the mice are observed for at least 14 days.

Electron Microscopy

A 10 μl of virus solution is placed on a FORMVAR/CARBON film for 1 minute and the residual solution is absorbed by using a filter paper. A 10 μl of 1–2% phosphotungstic acid is applied to the film, allowing to stain for 1 minute, and the residual solution is absorbed by using a filter paper. The virus is observed with a transmission electron microscopy (Hitachi H-7100).

C. Purification of Japanese Encephalitis Virus

For the purification of JEV from cell culture sources, a JEV containing sample is harvested from an infected cell culture.

For the purification of JEV from mouse brain sources, a JEV containing sample is obtained by subjecting the infected mouse brains to a preliminary treatment comprising the following procedures: adding 4×PBS (pH 8.0) to the harvested mouse brain and homogenizing the mixture; after centrifugation, adding to the homogenate protamine sulfate at a final concentration of 1.5 mg/ml for precipitation; allowing the resultant solution to stand for 2 hours at 4° C.; centrifuging and collecting the supernatant, which is then ready for further purification by the present process comprising the steps of microfiltration, ultrafiltration and liquid chromatography.

Microfiltration

Millipore filtration system, in cooperation with a Millidisk Hydrophilic Cartridge with 0.45 μm Durapore Membrane and a WATSON MARLOW 505S pump rotating at a speed of 40–80 rpm, is used to preliminarily remove cells and cell debris from a JEV containing sample obtained from JEV-infected cultured cells or mouse brain.

Ultrafiltration

Ultrafiltration has been described by A. S. Michael, in Progress in separation and purification (Perry, E. S. ed.) 1, 197–334, New York, John Wiley, 1968, which is incorporated herein by reference. Millipore Pellicon system in cooperation with Masterflex Easy-Load pump is used for the step of ultrafiltration. The sample is subjected to a recirculation filtration by filtering through a regenerated cellulose cassette with a predetermined molecular weight cutoff value at a flow rate of 1–3 liter/min in order to concentrate the viral particles.

Liquid Chromatography

The liquid chromatography is carried out via gel filtration, ion exchange chromatography or affinity column chromatography, in cooperation with Pharmacia FPLC system or BioCAD Perfusion Chromatography Workstation (Liapis, A. I., McCoy, M. A. (1992) Theory of perfusion chromatography, *J. Chromatoqr.,* 599, 87– 104; and Asenjo, J. A., Patrick, I. (1990) Large scale protein purification, in Protein purification application, E. L. V. Harris, S. Angal eds., IRL Press). The preferred conditions for operation, including buffer system used, flow rate and the like, are determined from the laboratory experiments and subject to utilization in the scale-up preparation of JE virus (Regnier, F. E. (1991), Perfusion chromatography, *Nature,* 350, 634–635).

Virus Inactivation

Formalin is added to a solution of purified virus in a volume ratio of 1:2000–4000 and the virus solution is stored at 4° C. for inactivation until no live virus can be detected. During the inactivation procedure, the plaque assay and the mouse IC challenge test as described above are used for examining the virus viability. After no abnormal event is observed in the tested animal, the inactivating step continues further for half of the time needed for the inactivation, thereby reaching the ending point of inactivation (Knight, C. A. (1975), Action of chemical and physical agents on viruses, in Chemistry of viruses, Springer-Verlag Wien, N.Y., 195–197).

RESULTS AND CONCLUSION

In the experiments, the tested JE virus samples include the reference vaccine (mouse brain), which is the JE vaccine Batch No. 184P prepared from the Beijing strain of JE virus obtained from the National Institute of Health (NIH) of Japan, and also the Beijing strain virus prepared from the mouse brains and cell cultures in the National Institute of Preventive Medicine, Taipei, Taiwan, R.O.C.

The virus recovery rate is determined by plaque assay. When the JE virus sample is subjected to microfiltration, the virus recovery is around 95–100%. Thereafter, ultrafiltration is carried out with a regenerated cellulose cassette having a molecular weight cutoff value of 300,000. The virus solution was concentrated for 42 times and about 85–95% of the undesired proteinaceous contaminants are removed at the step of ultrafiltration. The influence of flow rate upon ultrafiltration is summarized in Table 1, in which the recovery rate increases as the flow rate is reduced. When the flow rate was 1 liter/min, 90% of the virus recovery would be achieved.

TABLE 1

The correlation between the flow rate and the virus recovery in the ultrafiltration

| Flow rate (liter/min) | virus recovery (%) |
|---|---|
| 3 | 60 ± 5 |
| 2 | 65 ± 5 |
| 1 | 90 ± 5 |

The virus samples concentrated from the ultrafiltration are then subjected to liquid chromatography. The effects of gel filtration, ion exchange chromatography and affinity chromatography are described and compared below:

a) the concentrated (x42.5) virus suspension in an amount of 5% of the column volume is loaded onto a 26×700 mm gel filtration column packed with SEPHAROSE CL 6B and the column is developed with a 1/75 M phosphate buffer (pH 7.4) containing 0.85% NaCl at a linear flow rate of 5–15 cm/hr. Every 5 ml of the eluent is collected in one tube. The elution profile is shown in FIG. 1A;

b) 5 ml of the concentrated (x42.5) virus suspension is loaded onto a 10 mmD ×100 mmL (7.854 ml) ion exchange column packed with POROS HQ/M (PerSeptic Biosystems) and the column is developed with 40×column volume of a gradient established from 20 mM sodium phosphate buffer (pH 8.0) to 20 mM sodium phosphate buffer plus 2400 mM NaCl at a flow rate of 25 ml/min. Every 8 ml of the eluent is collected in one tube. The elution profile is shown in FIG. 1B; and c) 50 ml of the concentrated (×20) virus suspension is loaded onto a 44×160 mm (=250 ml) affinity column packed with Matrex Cellufine Sulfate (Amicon). The adsorption buffer is 1/75 M phosphate buffer plus 0.85% NaCl (pH 7.4) and the column is eluted with a desorption buffer of 1/75 M phosphate buffer plus 1.5 M NaCl (pH 7.4) at a flow rate of 10 ml/min. Every 13.5 ml of eluent was collected in one tube. The elution profile is shown in FIG. 1C.

The experimental data of the three liquid chromatography methodologies suggest that the gel filtration using SEPHAROSE CL-6B, in cooperation with Pharmacia FPLC system, gives the most effective effect for purification of JEV. Referring to FIG. 1A, four distinctive elution fractions are exhibited in the elution profile of gel filtration chromatography and the results of plaque assay show that about 90% of viral particles are obtained in the first peak and about 10% of viral particles are obtained in the second fraction. Bovine serum albumin is present mainly in the third fraction.

Figure 3:
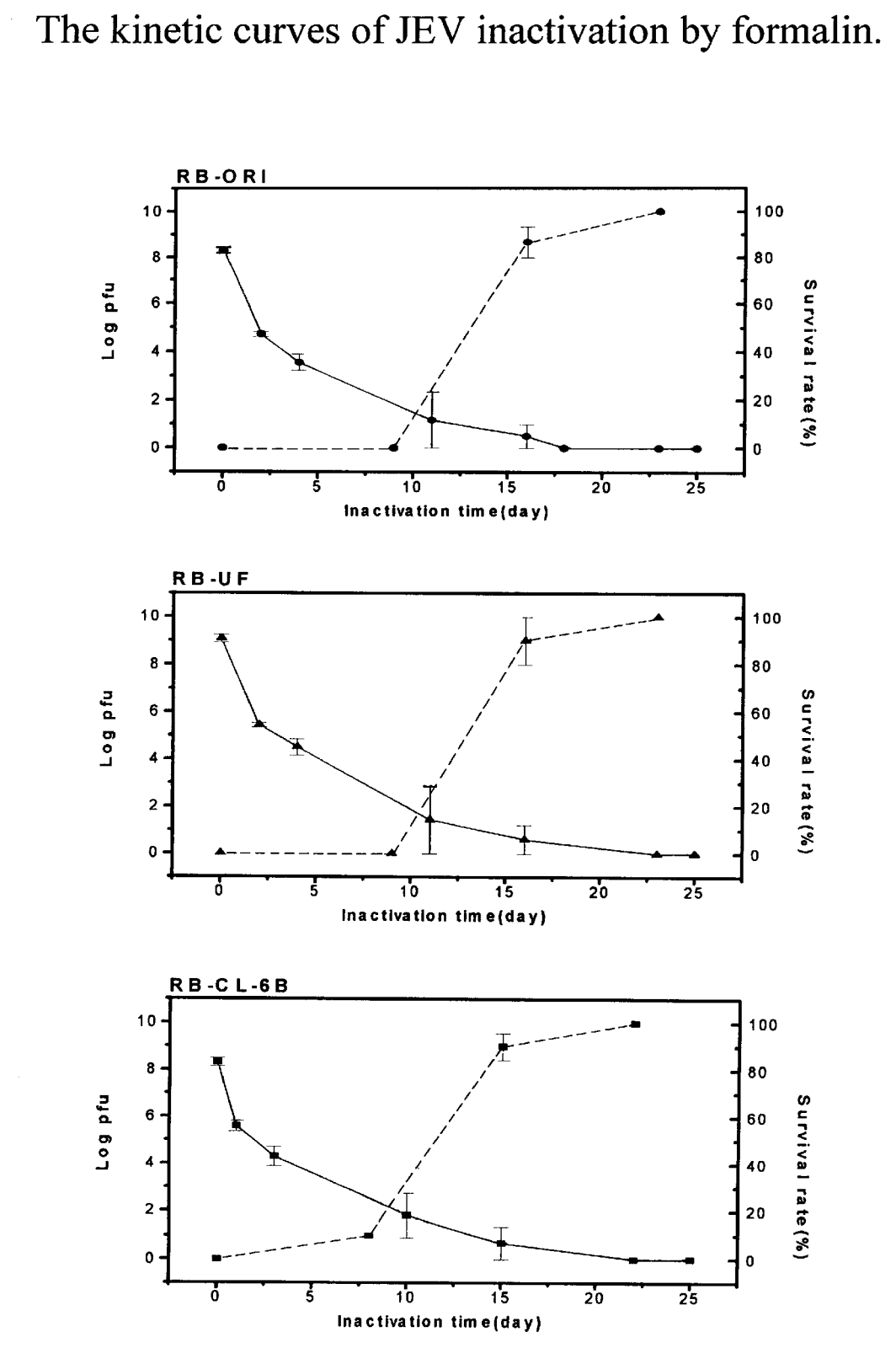

To inactivate the virus, formalin is added to the purified virus in a volume ratio of 1:2000. FIG. 3 shows the inactivation curve of JEV at each purification step. No plaque forms 33 days after formalin addition. Therefore, the inactivation step needs to be carried out for 50 days in order to reach the end point.

Figure 4:
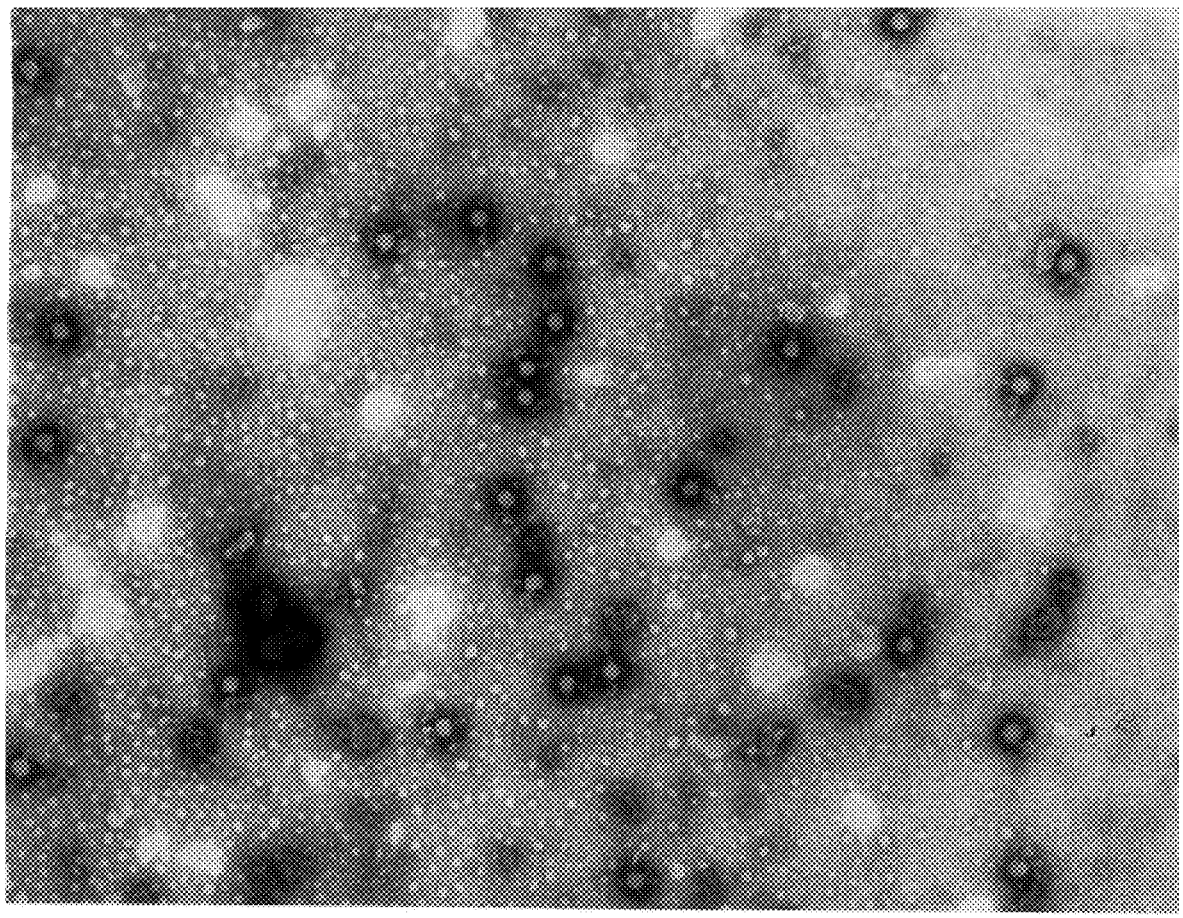
FIG. 4 shows the electron micrograph of JE virus purified by the method of the present invention.

From the electron microscopy, the virus is observed to be a substantially spherical particle having spikes present on the surface, and with a size of about 45–50 nm (FIG. 4).

Figure 5:
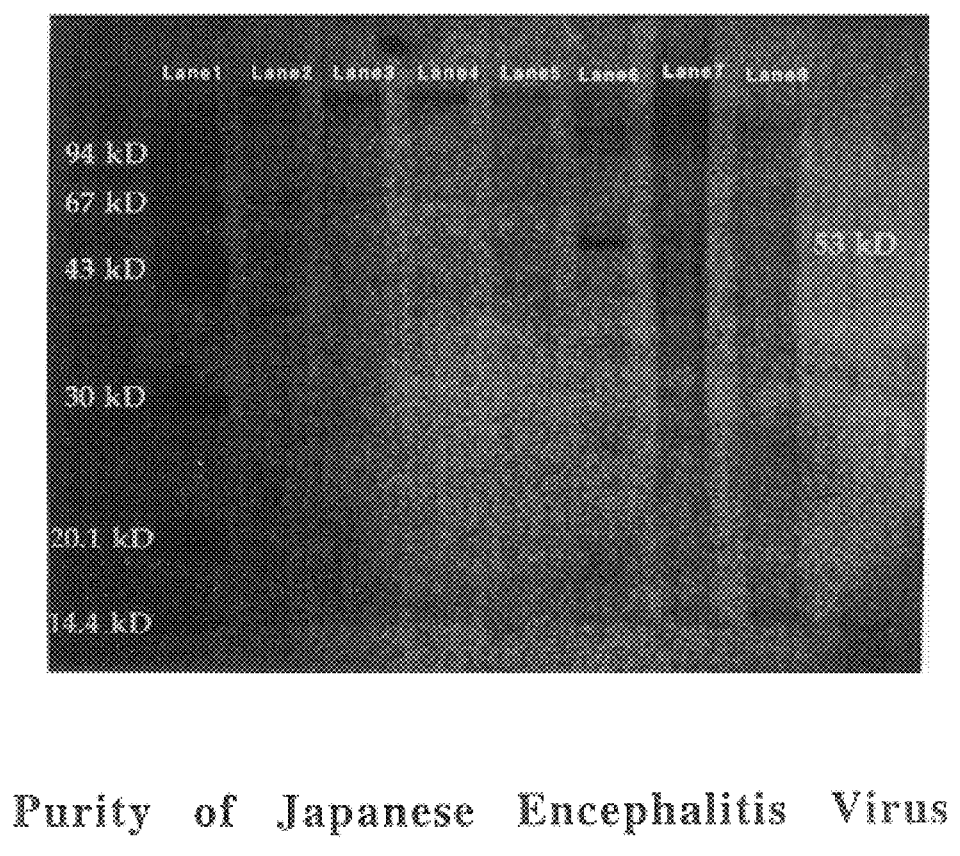
Figure 6A:
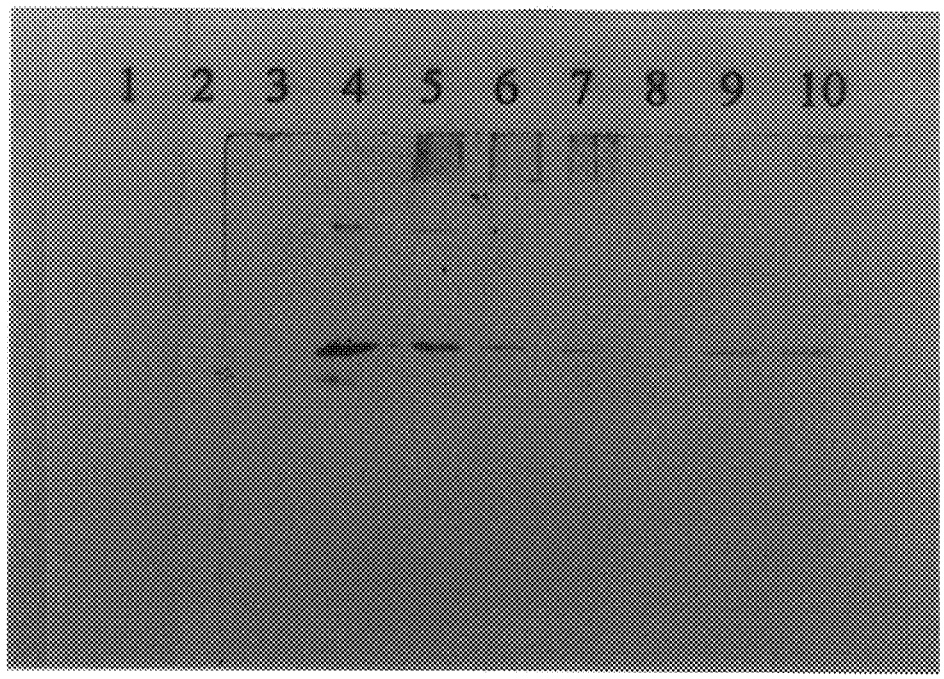
FIGS. 6A and 6B show the identity and purity of JE virus in various preparations, examined by Western Blotting with the use of pig anti-JEV antibody and goat anti-BSA antibody respectively.
Figure 6B:
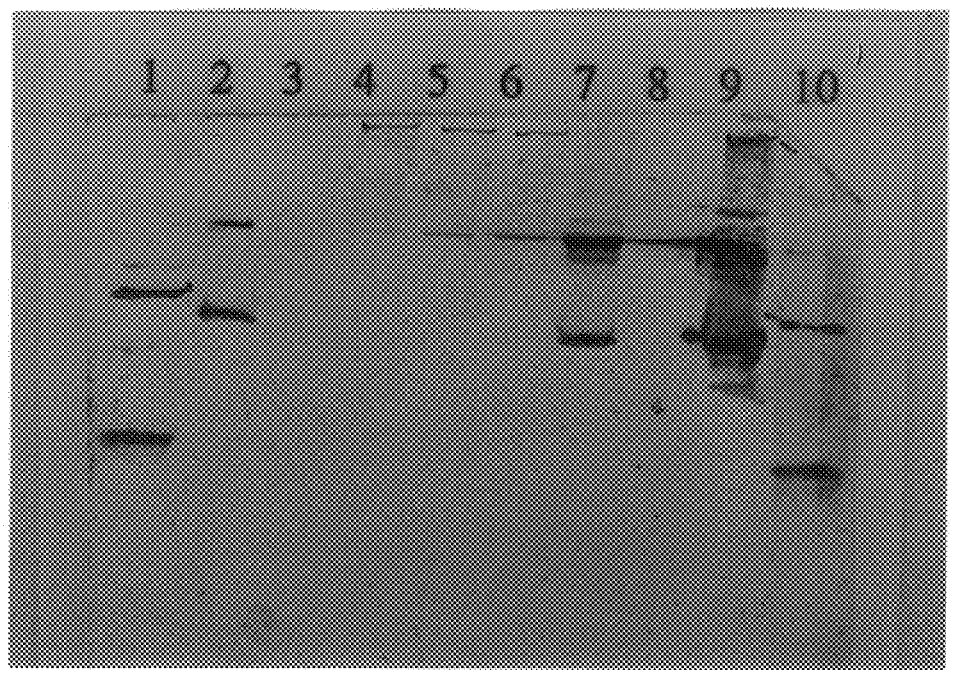

The purity and identity of the virus obtained from each purification step are examined by SDS-PAGE in combination with silver staining (FIG. 5) and Western Blotting (FIGS. 6A and 6B). Referring to FIG. 6A, pig anti-JEV antibodies are employed to determine the presence of viral coat protein and this serves as an indirect measure for determining the identity of the virus obtained from the liquid chromatography purification procedure, in which commercial vaccines are used for comparison (FIG. 6A, lanes 9 and 10). Residual proteins in the SEPHAROSE CL-6B peaks are determined by comparison with BSA, in which goat anti-BSA antibodies are employed (FIG. 6B).

In accordance with the standard promulgated by the WHO, the residual BSA contained in vaccine preparations derived from cell culture sources should not exceed 1 ppm (or 1 $\mu$g/ml). From the data shown in Table 2, the sequential purification procedure of the present process can eliminate at least 99% of BSA and the product obtained therefrom does comply with the requirements.

TABLE 2

The amount of residual BSA contained in each purification step

| Purification step | Amount of residual BSA |
|---|---|
| initial harvest of virus | 500 |
| microfiltration | 100 |
| ultrafiltration | 3–4 |
| liquid chromatography (gel filtration) | <0.001 |

The purification effects of microfiltration, ultrafiltration and gel filtration are summarized in Table 3.

TABLE 3

A comparison of the protein content and the recovery of virus in the virus solutions derived from each purification step

| Purification step | Volume (ml) | Protein content ($\mu$g/ml) | Virus titer (pfu/ml) | Recovery* (%) |
|---|---|---|---|---|
| initial harvest of virus | 2 × 10$^4$ | 300 ± 50 | (1 ± 0.5) × 10$^8$ | — |
| microfiltration | 2 × 10$^4$ | 300 ± 50 | (1 ± 0.5) × 10$^8$ | 100 |
| ultrafiltration | 4.7 × 10$^2$ | 800 ± 100 | (4 ± 0.5) × 10$^9$ | 90 ± 5 |
| LC (gel filtration) | 9.4 × 10$^2$ | 50 ± 10 | (2 ± 0.5) × 10$^9$ | 90 ± 5 |

*experimental six repeats.

Accordingly, JE vaccines could be prepared by following the protocol shown in Table 4.

Table 4. Preparation protocol of JE vaccine stock Virus-containing material from the Vero cell culture or mouse brain ---
Microfiltration
↓
Ultrafiltration
↓
Gel filtration
↓
Formalin inactivation
↓
Formulation & Immunoassay & Stability test
↓
Vaccine Bulk

---

From the above teachings, it is apparent that various modifications and variations can be made without departing from the spirit and scope of the present invention. It is therefore to be understood that this invention may be practiced otherwise than as specifically described.

What is claimed is:

1. An essentially pure live Japanese encephalitis virus preparation which is purified by the process comprising:
   a. obtaining a composition suitable for purification from a Japanese encephalitis virus-infected cell culture;
   b. removing cells and cell debris from said composition by microfiltration;
   c. conducting ultrafiltration directly on the product of step (b);
   d. subjecting the product of step (c) directly to gel filtration to obtain said pure live Japanese encephalitis virus preparation.

2. A Japanese encephalitis vaccine prepared by inactivating the essentially pure Japanese encephalitis virus preparation of claim 1.

3. The live Japanese encephalitis virus preparation of claim 1, wherein at least 99% of the contaminating proteinaceous substances have been removed and the virus recovery rate is at least 90%.

4. A process for large-scale purification of essentially pure live Japanese encephalitis virus preparation for use in vaccine preparation comprising:
   a. obtaining a composition suitable for purification from a Japanese encephalitis virus-infected cell culture or Japanese encephalitis virus-infected mouse brain tissue;
   b. removing cells and cell debris from said composition by microfiltration;
   c. conducting ultrafiltration directly on the product of step (b);
   d. subjecting the product of step (c) directly to gel filtration to obtain said pure live Japanese encephalitis virus preparation.

5. The process of claim 4, wherein the Japanese encephalitis virus-infected cell culture is selected from the group consisting of Japanese encephalitis virus-infected BHK21 cell culture, Japanese encephalitis virus-infected MK cell culture, Japanese encephalitis virus-infected Singh's *Aedes albopictus* cell culture, Japanese encephalitis virus-infected Vero cell culture, and Japanese encephalitis virus-infected C6/36 cell culture.

6. The process of claim 4, wherein said microfiltration is carried out with a 0.45 μm filtration membrane.

7. The process of claim 4, wherein said ultra-filtration step further removes substances having a molecular weight of no greater than about 3000 kDa.

8. The process of claim 4, wherein the ultra-filtration is a recirculation filtration.

9. The process of claim 4, wherein the flow rate of the ultra-filtration is from 1 to 3 liter/minute.

10. The process of claim 4, wherein the flow rate of the ultra-filtration is 1 liter/minute.

11. The process of claim 4, wherein the gel filtration is carried out in a column packed with a gel matrix having the capability to separate substances with a molecular weight within the range of from about 10 kDa to about 4000 kDa.

12. The process of claim 11, wherein said gel matrix is selected from the group consisting of SEPHAROSE CL-6B, SEPHAROSE CL-4B, SEPHAROSE CL-2B, SEPHAROSE 6B, SEPHAROSE 4B, SEPHAROSE 2B, SEPHACRYL S-400, SEPHACRYL S-300, SUPEROSE 6, ULTROGEL A2, ULTROGEL A4, and ULTROGEL A6.

13. The process of claim 11, wherein the gel filtration is carried out using phosphate buffered saline as elution buffer.

14. The process of claim 4, wherein said gel filtration is conducted at a linear flow rate of about 5 to about 15 cm/hour.

15. The process of claim 4, wherein the composition suitable as starting material for the purification process is obtained from Japanese encephalitis virus-infected Vero cell culture.

16. A method for preparing an essentially pure Japanese encephalitis virus vaccine comprising:

a. providing an essentially pure live Japanese encephalitis virus preparation which is purified by the process comprising:
   1. obtaining a composition suitable for purification from a Japanese encephalitis virus-infected cell culture or Japanese encephalitis virus-infected mouse brain tissue;
   2. removing cells and cell debris from said composition by microfiltration;
   3. conducting ultrafiltration directly on the product of step (2);
   4. subjecting the product of step (3) directly to gel filtration to obtain said pure live Japanese encephalitis virus preparation; and b. inactivating said live Japanese encephalitis virus preparation thereby producing a Japanese encephalitis virus vaccine.

17. The process of claim 16, wherein the composition suitable as starting material for the purification process is obtained from Japanese encephalitis virus-infected Vero cell culture.

* * * * *